United States Patent [19]

Potempa et al.

[11] Patent Number: 5,474,904
[45] Date of Patent: Dec. 12, 1995

[54] METHODS OF IMAGING CANCER CELLS USING MODIFIED C-REACTIVE PROTEIN

[76] Inventors: Lawrence A. Potempa, 1630 Montgomery Rd., Deerfield, Ill. 60015; John J. Kresl, 2602 Eastwood Ave., Apt. 1-F, Evanston, Ill. 60201; Byron E. Anderson, 5801 Reba, Morton Grove, Ill. 60053

[21] Appl. No.: 149,663

[22] Filed: Nov. 9, 1993

Related U.S. Application Data

[63] Continuation of Ser. No. 874,263, Apr. 24, 1992, Pat. No. 5,283,238.

[51] Int. Cl.[6] .................... G01N 33/534; G01N 33/574; G01N 33/58; A61K 35/16
[52] U.S. Cl. .................... 435/7.23; 435/968; 435/7.9; 436/504; 436/64; 436/804; 436/813; 424/1.57; 424/9.2; 424/9.6
[58] Field of Search .................... 435/7.23, 7.9; 436/64, 813; 424/1.57, 9

[56] References Cited

U.S. PATENT DOCUMENTS

| | | | |
|---|---|---|---|
| 4,444,744 | 4/1984 | Goldenberg | 424/1.49 |
| 4,816,402 | 3/1989 | Rosen et al. | 530/388.8 |
| 4,857,314 | 8/1989 | O'Connor et al. | 424/85.1 |

FOREIGN PATENT DOCUMENTS

WO89/09628  10/1989  WIPO.

OTHER PUBLICATIONS

Barna et al., *Cancer Research*, 47:3959–3963 (1987).
Barna et al., *Cancer Research*, 44:305–310 (1984).
Barna et al., *FASEB J.*, 2274a (1983).
Barna et al., *J. Biol. Resp. Mod.*, 7:483–487 (1988).
Barna et al., *FASEB J.*, 6:1433a (1992).
Bravo et al., *J. Rheumatology*, 8:291–294 (1981).
Bray et al., *Clin. Immunol. Newsletter*, 8:137–140 (1987).
Chu et al., *Proc. Amer. Acad. Cancer Res.*, 28:344a (1987).
Chu et al., *Proc. Am. Acad. Cancer Res.*, 29:371a (1988).
Chu et al., *Proc. Am. Acad. Cancer Res.*, 30:333a (1989).
Chudwin et al., *J. Allergy Clin. Immunol.*, 77:216a (1986).
de Beer et al., *J. Immuno. Meth.*, 50:17–31 (1982).
Deodhar et al., *J. Biol. Resp. Modifiers*, 1:27–34 (1982).
Deodhar et al., *Cleveland Clinic Quarterly*, 53:223–234 (1986).
Deodhar et al., *Cancer Research*, 42:5084–5088 (1982).
Doedhar et al., *Proc. Am. Assoc. Cancer Research*, 32:404 (1991).
Deodhar et al., *FASEB J.*, 3:831a (1989).
Dixon et al., *Scand. J. Rheumatology*, 13:39–44 (1984).
Gautam et al., *J. Biol. Res. Modifiers*, 8:560–569 (1989).
Hawkes et al., *Analyt. Biochem.*, 119:142–47 (1982).
Hornung, *Proc. Soc. Exp. Biol. Med.*, 139:1166–1169 (1972).
Guedson et al., *J. Histochem. Cytochem.*, 27:1131–45 (1981).
Hu et al., *Biochem.*, 25:7834–39 (1986).
Hu et al., *J. Biol. Chem.*, 635: 1500–04 (1988).
Kaplan et al., *Meth. Enzymol.*, 172:393–399 (1989).
Kendall et al., *J. Immunol. Meth.*, 56:329–39 (1983).
Kilpatrick et al., *Immunol. Res.*, 10:43–53 (1991).
Krakoff, *CA–A Cancer Journal for Clinicians*, 41:264–278 (1991).
Laemmli, *Nature*, 227:680–685 (1970).
Lei et al., *J. Biol. Chem.*, 260:13377–13383 (1985).
MacDonald et al., *Biochim. Biophys. Acta*, 1061:297–301 (1991).
Mantzouranis et al., *Ped. Res.*, 18:260a (1984).
McIntosh et al., *Cancer Research*, 49:1408–1414 (1989).
Oku et al., *Biochim. Biophys. Acta*, 691:332–340 (1982).
Olson et al., *Biochim. Biophys. Acta*, 557:9–23 (1979).
Osmand et al., *Proc. Natl. Acad. Sciences, U.S.A.*, 74:739–743 (1977).
Pappas et al., *J. Immunol. Meth.*, 64:205–14 (1983).
Pepys et al., *Advances in Immunology*, 34:141–212 (1983).
Potempa et al., *Inflammation*, 12:391–405 (1988).
Potempa et al., *Mol. Immunol.*, 20:1165–1175 (1983).
Potempa et al., *Mol. Immunol.*, 24:531–541 (1987).
Potempa et al., *Proc. Amer. Acad. Cancer Res.*, 28:344a (1987).
Potempa et al., *FASEB J.*, 2:731a (1988).
Potempa et al., *Protides Biol. Fluids*, 34:287–290 (1986).
Radosevich et al., *Cancer Research*, 46:5808–5812 (1985).
Rees et al., *Fed. Proc.*, 45:263a (1986).
Rizk et al., *Cancer*, 58:55–61 (1986).
Samols et al., *Biochem. J.*, 227:759–65 (1985).
Samols et al., *Protides Biol. Fluids*, 34:263–66 (1986).
Sorenson et al., *Experientia*, 42:161–162 (1986).
Thomassen et al., *FASEB J.*, 6:1151a (1992).
Thombre et al., *Cancer Immunol. Immunother.*, 16:145–150 (1984).
Tillett and Francis, *J. Exp. Med.*, 52:561–71 (1930).
Vigushin et al., *J. Clin. Invest.*, 91:1351–57 (1993).
Volanakis et al., *J. Immunol.*, 113:9–17 (1974).
Volanakis et al., *J. Immunol.*, 126:1820–1825 (1981).
Walker et al., *J. Clin. Path.*, 37:1022–1026 (1984).
Wang et al., *J. Biol. Chem.*, 257:13610–13615 (1982).
Weiss, *Clinical and Experimental Metastasis*, 7:127–167 (1989).

(List continued on next page.)

*Primary Examiner*—Toni R. Scheiner
*Assistant Examiner*—Nancy J. Parsons
*Attorney, Agent, or Firm*—Willian Brinks Hofer Gilson & Lione

[57] ABSTRACT

The invention provides a method of treating cancer in a mammal comprising administering to the mammal an effective amount of modified C-reactive protein ("mCRP"). The invention also provides a method of treating cancer in a mammal comprising administering to the mammal mCRP in combination with another agent such as a chemotherapeutic compound, immunoadjuvant, or cytokine. The mCRP may be administered to the mammal in a pharmaceutically-acceptable carrier or in liposomes. The invention further provides a method of identifying cancer cells in a mammal using mCRP as an imaging agent.

5 Claims, 5 Drawing Sheets

OTHER PUBLICATIONS

Whitehead et al., *Biochem. J.,* 266:283–290 (1990).
Woo et al., *J. Biol. Chem.,* 260:13384–88 (1985).
Wood et al., *J. Clin. Invest.,* 30:616–622 (1951).
Ying et al., *J. Immunol.,* 143:221–28 (1989).

Zahedi et al., *Cancer Research,* 46:5077–5083 (1986).

Zeller et al., *Fed. Proc.,* 46:1033a (1987).

Shields, M. J., et al., *J. Immunol Methods,* vol. 141, No. 2, pp. 253–262, 1991.

| GROUP | 5-FU | BUFFER | DAY 6 BODY WEIGHTS | MEAN LIFE SPAN |
|---|---|---|---|---|
| GROUP 1 | 0 | 0 | 16.8 g | 20 DAYS |
| GROUP 2 | 0 | LOW DOSE BUFFER | ≈ GROUP 1 | ≈ GROUP 1 |
| GROUP 3 | 0 | HIGH DOSE BUFFER | ≈ GROUP 1 | ≈ GROUP 1 |
| GROUP 4 | 20 mg/kg | 0 | 20% DECREASE FROM DAY 2 | ≈ GROUP 1 |

| GROUP | 5-FU | mCRP DOSE | DAY 6 BODY WEIGHTS | MEAN LIFE SPAN |
|---|---|---|---|---|
| GROUP 5 | 0 | 50 μg | ≈ DAY 2 | ≈ CONTROL |
| GROUP 6 | 0 | 200 μg | ≈ DAY 2 | ≈ CONTROL |
| GROUP 7 | 20 mg/kg | 50 μg | 10% DECREASE FROM DAY 2 | 40% DECREASE FROM CONTROL |
| GROUP 8 | 20 mg/kg | 200 μg | 10% DECREASE FROM DAY 2 | ≈ CONTROL |
| GROUP 9 | 10 mg/kg | 50 μg | ≈ CONTROL | 128% INCREASE FROM CONTROL |
| GROUP 10 | 10 mg/kg | 200 μg | ≈ CONTROL | 133% INCREASE FROM CONTROL |

METHODS OF IMAGING CANCER CELLS USING MODIFIED C-REACTIVE PROTEIN

This application is a continuation of application Ser. No. 07/874,263, filed Apr. 24, 1992, U.S. Pat. No. 5,283,238.

FIELD OF INVENTION

The invention relates to methods of treating cancer with modified C-reactive protein ("mCRP"). The invention also relates to the use of mCRP as an imaging agent to identify cancer cells in mammals.

BACKGROUND OF THE INVENTION

It has been estimated that approximately 400,000 deaths each year in the United States are attributable to cancer. It appears that there is no single determinant of cancer cell growth and metastasis. Rather, the propensity of cancer cells to proliferate and metastasize is the sum total of numerous cellular characteristics, and individual cancer cells may use different mechanisms to achieve the same result [Weiss, *Clinical and Experimental Metastasis*, 7:127–167 (1989)].

While therapeutic strategies such as surgery, chemotherapy, and radiation therapy have improved in recent years [See, e.g., Krakoff, *CA-A Cancer Journal for Clinicians*, 41:264–278 (1991)], a substantial number of cancers are resistant to therapy and ultimately cause the death of the patient. Thus, a need emerges to discover new and useful means of cancer therapy.

CRP STRUCTURE AND ACTIVITY

C-reactive protein was first described by Tillett and Francis [*J. Exp. Med.*, 52:561–71 (1930)] who observed that sera from acutely ill patients precipitated with the C-polysaccharide of the cell wall of *Streptococcus pneumonia*. Other investigators subsequently identified the reactive serum factor as protein, hence the designation "C-reactive protein" or "CRP." Kilpatrick et al., *Immunol. Res.*, 10:43–53 (1991), provides a recent review of CRP.

CRP is a pentameric molecule which consists of five identical subunits [Osmand et al., *Proc. Natl. Acad. Sciences, U.S.A.*, 74:739–743 (1977)]. This pentameric form of CRP is sometimes referred to as "native CRP."

The gene sequence for human CRP has been cloned [Lei et al., *J. Biol. Chem.*, 260:13377–13383 (1985)]. In addition, the primary sequences for rabbit CRP [Wang et al., *J. Biol. Chem.*, 257:13610–13615 (1982)] and murine CRP have been reported [Whitehead et al., *Biochem. J.*, 266:283–290 (1990)], and is under investigation for rat, dog, horse, goat, and sheep. Clinical and laboratory observations have determined that the acute phase response, classically defined by the well-defined changes of the blood [Pepys et al., *Advances in Immunology*, 34:141–212 (1983)], develops during various states of disease and injury including malignant neoplasia, ischemic necrosis, and bacterial, viral, or fungal parasitic infections. Measurement of serum acute phase reactants such as CRP have been utilized in clinical tests for diagnosis and clinical management of patients with various conditions, including systemic lupus erythematosus (SLE) [Bravo et al., *J. Rheumatology*, 8:291–294 (1981)], rheumatoid arthritis [Dixon et al., *Scand. J. Rheumatology*, 13:39–44 (1984)], graft versus host disease [Walker et al., *J. Path.*, 37:1022–1026 (1984)], as well as many other diseases.

Activities of CRP in vitro against tumor cells has been investigated. For example, Hornung discloses that CRP added with lymphocytes inhibited growth of human melanoma cells after 72 hours of culture [Hornung, *Proc. Soc. Exp. Biol. Med.*, 139:1166–1169 (1972)]. Hornung also discloses that the CRP was toxic to the lymphocytes in the cell culture.

Barna et al., *Cancer Research*, 44:305–310 (1984) describe in vitro studies relating to effects of multilamellar vesicles containing human CRP on murine macrophage activation. Barna et al. report that murine macrophages phagocytosed the multilamellar vesicles containing CRP and, after exposure to the vesicles, displayed enhanced production of superoxide anion and increased anti-tumor activity against syngeneic murine T241 fibrosarcoma, syngeneic murine B-16 melanoma cells, and allogeneic murine Sarcoma-1 cells. The anti-tumor activity was also generated in vivo using a Winn neutralization assay. [See also, Barna et al., *FASEB J.*, 2274a (1983)]. Barna et al. also report that non-encapsulated CRP enhanced macrophage superoxide anion activity in vitro, but only in concentrations 10 to 100 times greater than the multilamellar encapsulated dose. Gautam et al., *J. Biol. Res. Modifiers*, 8:560–569 (1989), teach that the anti-metastatic effect of multilamellar vesicles containing human CRP may involve cells bearing T and/or NK cell markers in addition to macrophages.

Zahedi et al., *Cancer Research*, 46:5077–5083 (1986), disclose that purified human CRP is capable of mediating activation of macrophages to a tumoricidal state in vitro. The authors teach that when elicited macrophages were exposed to human CRP for thirty minutes to 2 hours, tumoricidal activity was induced against the murine P815 mastocytoma cell line, the murine L-929 fibroblast carcinoma cell line, and the human CAK-1 carcinoma cell line. Zahedi et al. also teach that when CRP was heat-aggregated at 85° C. for 1 hour prior to measuring tumoricidal activity, the CRP had significantly less killing activity than CRP that had not been heat-aggregated. Zahedi et al. disclose that no synergistic effect was shown by CRP when combined with a lymphokine.

Barna et al., *J. Biol. Resp. Mod.*, 7:483–487 (1988), disclose that exposure of human alveolar macrophages to purified human CRP in vitro enhanced macrophage cytotoxicity against human SK-MEL-28 melanoma cells and human CRL 1718 astrocytoma cells. Barna et al. also teach that macrophage responsiveness to CRP may be adversely affected by smoking.

Thomassen et al., *FASEB J.*, 6:1151a (1992), disclose in vitro modulation of tumoricidal activity of human monocytes and human alveolar macrophages by a synthetic peptide derived from CRP. Thomassen et al. report that monocytes treated with a synthetic peptide showed greater than or equal to 2-fold enhancement of Tumor Necrosis Factor (TNF) and IL-1 secretion, whereas alveolar macrophages showed no enhanced secretion of either TNF or IL-1.

Barna et al., *Cancer Research*, 47:3959–3963 (1987), disclose that exposure of human peripheral blood monocytes to acute phase quantities of human CRP in vitro resulted in elevated superoxide anion production and in cytotoxicity against human astrocytoma cells. Barna et al. also disclose that the CRP-induced cytotoxicity was inhibited by phosphorylcholine. The authors suggest that CRP activation may be associated with CRP binding to a component of human serum.

Several in vivo studies relating to the effects of CRP on tumor growth have been conducted. For instance, Rizk et al.,

*Cancer,* 58:55–61 (1986), describe effects of rabbit CRP and the polycation, poly-L-arginine (PLA), on the V×2 carcinoma cell line in rabbits. Rizk et al. teach that CRP had no antitumor effect in vivo in the absence of PLA.

O'Connor et al., U.S. Pat. No. 4,857,314 disclose a method for treating Meth A sarcoma in animals or humans by administering tumor necrosis factor (TNF) in combination with purified human C-reactive protein to enhance the tumoricidal activity of the TNF. O'Connor et al. teach that human CRP, administered alone, had only minimal or slight antitumor activity.

Deodhar et al., *Cancer Research*, 42:5084–5088 (1982), describe activity of multilamellar vesicles containing human CRP in vivo against murine fibrosarcoma, T241, lung metastases. Deodhar et al. report that animals treated with intravenous injections of multilamellar vesicles containing CRP after T241 primary tumors were excised had fewer and smaller lung metastases. Deodhar et al. also report that encapsulation of CRP in multilamellar vesicles greatly enhanced the anti-metastatic effects, since free (nonencapsulated) CRP administered in a dose 40 times higher than that given with multilamellar vesicles, did not show a comparable effect [Id., See also, Deodhar et al., *Cleveland Clinic Quarterly*, 53:223–234 (1986)].

Thombre et al., *Cancer Immunol. Immunother.,* 16:145–150 (1984), describe anti-metastatic activity of multilamellar vesicles containing human CRP against a murine colon adenocarcinoma (MCA-38). Thrombre et al. report that animals treated with multilamellar vesicles containing CRP, administered parenterally after the growth of the primary tumor, showed fewer liver metastases and longer survival as compared to control animals. Id.

Deodhar et al. also describe anti-tumor effects of multilamellar vesicles containing a synthetic peptide derived from CRP [Deodhar et al., *Proc. Am. Assoc. Cancer Research,* 32:404 (1991)]. However, Deodhar et al. report that administering comparable doses of non-encapsulated synthetic peptide was ineffective [Id.]. Barna et al., *Proc. Am. Assoc. Cancer Research,* 32:237 (1991), suggest that the antitumor activity demonstrated in the T241 lung metastatic model may result from enhanced infiltration of MAC 1+ cells from the blood into the lung.

Deodhar at al., *FASEB J.,* 3:831a (1989), further describe activity of purified human CRP or a peptide fragment in combination with IL-2 against murine fibrosarcoma T241 lung metastases. Deodhar et al. report that administering a combination of $1 \times 10^4$ U IL-2 and CRP or a peptide fragment was more effective than administering $5 \times 10^4$ U IL-2. Barna et al. disclose in vitro cytolytic data that suggests that the combination of CRP peptide fragment and IL-2 augments human monocyte activity but not natural killer (NK) activity [*FASEB J.,* 6:1433a (1992)].

MODIFIED-CRP STRUCTURE AND ACTIVITY

In about 1983, another form of CRP was discovered which is referred to as "modified C-reactive protein" or "mCRP." mCRP has significantly different charge, size, solubility and antigenicity characteristics as compared to native CRP [Potempa et al., *Mol. Immunol.,* 20:1165–75 (1983)]. mCRP also differs from native CRP in its binding characteristics. For instance, mCRP does not bind phosphorylcholine [Id.; Chudwin et al., *J. Allergy Clin. Immunol.,* 77:216a (1986)].

The distinctive antigenicity of mCRP has been referred to as "neo-CRP." Neo-CRP antigenicity is known to be expressed on:

1) CRP treated with acid, urea or heat under certain conditions;
2) the primary translation product of DNA coding for human and rabbit CRP; and
3) CRP immobilized on plastic surfaces

[Potempa et al., *Mol. Immunol.,* 20:1165–75 (1983); Mantzouranis et al., *Ped. Res.,* 18:260a (1984); Samols et al., *Biochem. J.,* 227:759–65 (1985); Potempa et al., *Mol. Immunol.,* 24:531–541 (1987)]. A molecule reactive with polyclonal antibody specific for neo-CRP has been identified on the surface of 10–25% of peripheral blood lymphocytes (predominantly NK and B cells), 80% of monocytes, and 60% of neutrophils, and as well as at sites of tissue injury [Potempa et al., *FASEB J.,* 2:731a (1988); Bray et al., *Clin. Immunol. Newsletter,* 8:137–140 (1987); Rees et al., *Fed. Proc.,* 45:263a (1986)].

Furthermore, mCRP differs from native CRP in its biological activity. It has been reported that mCRP can influence the development of monocyte cytotoxicity, improve the accessory cell function of monocytes, potentiate aggregated-IgG-induced phagocytic cell oxidative metabolism, and increase the production of interleukin-1, prostaglandin E and lipoxygenase products by monocytes [Potempa et al., *Protides Biol. Fluids,* 34:287–290 (1987); Potempa et al., *Inflammation,* 12:391–405 (1988); Chu et al., *Proc. Amer. Acad. Cancer Res.,* 28:344a (1987); Potempa et al., *Proc. Amer. Acad. Cancer Res.,* 28:344a (1987); Zeller et al., *Fed. Proc.,* 46:1033a (1987); Chu et al., *Proc. Amer. Acad, Cancer Res.,* 29:371a (1988)].

In vivo experiments with mCRP were performed to determine if mCRP was capable of providing a protective effect against lethal doses of *Streptococcal pneumonia* [Chudwin et al., *J. Allergy Clin. Inmmunol.,* 77:216a (1986)]. These studies demonstrated that intravenous administration of mCRP not only protected the animals from lethal *S. pneumonia* doses but that mCRP efficacy was 3 to 4 fold greater than native CRP.

mCRP can also be used to bind immune complexes, as disclosed in co-pending U.S. application Ser. No. 07/582,884, filed Oct. 3, 1990. This application was filed as a national application of PCT application U.S. Ser. No. 89/01247 (published as WO 89/09628 on Oct. 19, 1989) and is a continuation-in-part of U.S. application Ser. No. 07/176,923, filed Apr. 4, 1988, now abandoned. Further, mCRP is useful in treating viral infections such as human immunodeficiency virus 1 ("HIV-1"), as disclosed in co-pending U.S. application Ser. No. 07/799,448, filed Nov. 27, 1991. Finally, mCRP can be used in treating non-streptococcal bacterial infections and endotoxin sepsis, as disclosed in co-pending U.S. application Ser. No. 07/800,508, filed Nov. 27, 1991.

In in vitro studies, mCRP has been found to suppress or enhance the development of tumoricidal function in monocytes depending on the material used to elicit the antitumoricidal monocytes [Chu et al., *Proc. Am. Acad. Cancer Res.,* 29:371a (1988); Chu et al., *Proc. Am. Acad. Cancer Res.,* 30:333a (1989)]. To Applicants' knowledge, there have been no reports on anti-cancer activity of mCRP in vivo. Moreover, Applicants are not aware of any reports of mCRP being used to treat cancer in mammals.

SUMMARY OF THE INVENTION

The invention provides a method of treating cancer in a mammal comprising administering to the mammal an effective amount of modified-CRP in a pharmaceutically-acceptable carrier.

The invention also provides a method of treating cancer in a mammal comprising administering to the mammal a plurality of liposomes collectively containing an effective amount of modified-CRP.

The invention also provides a method of treating cancer in a mammal comprising administering to the mammal modified-CRP in combination with another agent, both being administered in amounts sufficient so that the combination is effective against the cancer.

The invention further provides a method of identifying cancer cells in a mammal using an imaging agent comprising modified-CRP. To do so, labeled modified-CRP may be administered and detected in the mammal. Alternatively, a labeled component that binds modified-CRP may be administered and detected in the mammal.

DETAILED DESCRIPTION OF THE PRESENTLY PREFERRED EMBODIMENTS

The present invention provides methods for treating cancer using modified C-reactive protein ("mCRP"). The mCRP useful in the practice of the present invention may be from any species. There is substantial homology between the amino acid sequences of C-reactive protein ("CRP") from different species. For instance, there is from about 50% to about 80% sequence homology between CRP from various mammalian species. Hu et al., *Biochem.*, 25:7834–39 (1986); Whitehead et al., *Biochem. J.*, 266:283–90 (1990); Kilpatrick et al., *Immunol. Res.*, 10:43–53 (1991). It is, therefore, expected that mCRP from any species will be effective in treating cancer. Thus, a mammal having cancer may be treated with mCRP from a different species (e.g., mice can be treated with human mCRP). Alternatively, and preferably, the mammal is treated with homologous mCRP (e.g., humans are treated with human mCRP) to avoid immune reactions to the mCRP.

mCRP is preferably made using native CRP as a starting material. Methods of isolating CRP from natural sources are known in the art and are described, for example, by Volanakis et al., *J. Immunol.*, 113:9–17 (1978); de Beer et al., *J. Immunol. Meth.*, 50:17–31 (1982); Potempa et al., *Mol. Immunol.*, 24:531–541 (1987). CRP is preferably isolated from pleural or ascites fluid by calcium-dependent affinity chromatography using phosphorylcholine-substituted Bio-Gel A 0.5 m (an agarose-based resin obtained from BioRad Laboratories, Richmond, Calif.) [See, Potempa et al., *Mol. Immunol.*, 24:531–541 (1987)]. This CRP isolation method is further described in Example 1 below. Using this isolation method, CRP can be obtained which is about 99% pure.

Genomic and cDNA clones coding for human, mouse, and rabbit CRP have been isolated. Lei et al., *J. Biol. Chem.*, 260:13377–83 (1985); Woo et al., *J. Biol. Chem.*, 260:13384–88 (1985); Hu et al., *Biochem.*, 25:7834–39 (1986); Hu et al., *J. Biol. Chem.*, 263:1500–1504 (1988); Whitehead et al., *Biochem. J.*, 266:283–90 (1990). Given the substantial homology between CRP from different species, probes can readily be prepared so that genomic and cDNA clones can be isolated which code for CRP from other species. Methods of preparing such probes and isolating genomic and cDNA clones are well known in the art. See, e.g., Lei et al., *J. Biol. Chem.*, 260:13377–83 (1985); Woo et al., *J. Biol. Chem.*, 260:13384–88 (1985); Hu et al., *Biochem.*, 25:7834–39 (1986); Hu et al., *J. Biol. Chem.*, 263:1500–1504 (1988); Whitehead et al., *Biochem. J.*, 266:283–90 (1990). Using one of the known clones or a newly-isolated clone, CRP can be prepared using conventional and well known recombinant DNA techniques and cell culture and fermentation conditions. See, e.g., Hu et al., *J. Biol. Chem.*, 263:1500–1504 (1988). However, to obtain pentameric native CRP, eukaryotic host cells, preferably mammalian host cells, should be used. See Samols et al., *Protides Biol. Fluids*, 34:263–66 (1986); Hu et al., *J. Biol. Chem.*, 263:1500–1504 (1988).

Methods of making mCRP from CRP are also known in the art [See, e.g., Potempa et al., *Mol. Immunol.*, 20:1165–1175 (1983)]. For instance, mCRP can be prepared by denaturing CRP. CRP can be denatured by treatment with an effective amount of urea (preferably 8M) in the presence of a conventional chelator (preferably ethylenediamine tetraacetic acid (EDTA) or citric acid). Further, CRP can be treated to produce mCRP by adjusting the pH of the protein to below about 3 or above about 11–12. Finally, mCRP can be produced by heating CRP above 50° C. for a time sufficient to cause denaturation (preferably at 63° C. for 2 minutes) in the absence of calcium or in the presence of a chelator such as those listed above.

mCRP can also be prepared using recombinant DNA techniques. The primary translation product of the CRP gene (preCRP) has been found to express neo-CRP antigenicity [Mantzouranis et al., *Ped. Res.*, 18:260a (1984)]. Accordingly, mCRP can be prepared by selecting conditions so that the CRP subunits are not assembled into pentameric native CRP in the host cell. This can be accomplished by expressing the desired genomic or cDNA clone in a prokaryotic host. See Samols et al., *Prot. Biol. Fluids*, 34:263–66 (1986). The mCRP produced in this manner appears to consist of aggregates of CRP subunits and/or preCRP and perhaps other CRP peptides. See Id. This form of mCRP is insoluble, and further purification is problematical. However, it should be possible to inject this insoluble material into mammals as a suspension without further processing, since an aggregated form of serum-purified mCRP has been shown to be effective, as described further in Example 4 below.

mCRP may be distinguished from native CRP by several criteria. As noted in the Background section, modified CRP expresses neo-CRP antigenicity, whereas native CRP does not. Neo-CRP antigenicity can be detected using polyclonal antisera specific for neo-CRP [See, Potempa et al., *Mol. Immunol.*, 24:531–541 (1987)]. Preferably, however, mCRP is distinguished from native CRP using monoclonal antibodies like those described in co-pending application Ser. No. 07/374,166, the disclosure of which is incorporated herein by reference. Hybridomas secreting the monoclonal antibodies disclosed in the co-pending application are deposited with the American Type Culture Collection, Rockville, Md., and are registered as HB10175 (mAb 15.2C10), HB10176 (mAb 26.8C10), HB10177 (mAb 13.3H12), and HB10178 (mAb 15.1D6). These monoclonal antibodies are also described in Ying et al., *J. Immunol.*, 143:221–28 (1989). The antisera and antibodies can be used, for example, in ELISA assays, and preferably in Dot-ELIFA assays described in Example 1, part C, below, to distinguish mCRP from native CRP.

Another basis on which to distinguish mCRP from native CRP is that mCRP binds immune complexes and aggregated immunoglobulin, whereas native CRP does not as described in co-pending application Ser. No. 07/582,884 and published PCT application WO 89/09628. In addition, mCRP may be distinguished from native CRP on the basis of charge, solubility, binding characteristics and biological activity as referenced in the Background section. However, to show that a preparation contains mCRP, it is usually sufficient to establish that the preparation 1) reacts positively with an antibody specific for an epitope found only on mCRP or 2) binds aggregated immunoglobulin (e.g., aggregated IgG).

Although not wishing to be bound by any particular theory, it is believed that mCRP is formed by the dissociation of the five CRP subunits, each of which then undergoes a spontaneous conformational change to form mCRP. See Bray et al., *Clin. Immunol. Newsletter*, 8:137–140 (1987). Accordingly, it is possible that fragments of the CRP subunits may have the same activities described herein for mCRP, and the use of such fragments is considered to come within the scope of the present invention.

It is also believed that proteins substantially homologous to CRP will have the activities described herein for mCRP, and such proteins are also considered to come within the scope of the present invention. For instance, CRP subunits having certain amino acids added, deleted or substituted by, e.g., site-directed mutagenesis of the CRP gene, would likely be effective in the treatment of cancer and could be substituted for mCRP. In particular, mCRP is defined herein to include the primary translation product of the CRP gene.

In accordance with a first method of treating cancer in a mammal, an effective amount of mCRP is administered to the mammal. The term "cancer" in the present invention is used in a broad sense and refers to the physiological condition in mammals that is usually characterized by unregulated cell growth. It is contemplated that mCRP may be used to treat a variety of cancers, including but not limited to, adenocarcinoma, lymphoma, fibrosarcoma, and leukemia. The mCRP may be administered to the mammal when the presence of cancer cells in the mammal is first detected or before the cancer becomes too serious. Alternatively, the mCRP may be administered after the cancer progresses so as to reduce metastasis of cancer cells, to reduce metastatic tumors, or to reduce primary tumor burden.

mCRP may be administered to the mammal in a pharmaceutically-acceptable carrier. Pharmaceutically-acceptable carriers are well known to persons skilled in the art. For instance, suitable carriers for administering mCRP include fluids such as water, saline, and buffer. More preferably, a Tris or phosphate buffered saline is used as the carrier. It will be apparent to those persons skilled in the art that certain carriers may be more preferable depending upon, for instance, the route of administration and concentration of protein being administered.

Alternatively, a plurality of liposomes collectively containing an effective amount of mCRP may be administered to the mammal. The term "liposome" in the present invention relates to any sac-like or hollow vesicle-like structure which is capable of encapsulating mCRP, and includes but is not limited to, multilamellar vesicles, unilamellar vesicles, and red blood cell ghosts. Methods of preparing liposomes and encapsulating molecules in liposomes are well known in the art.

Preferably, the liposomes containing mCRP are unilamellar vesicles formed by extrusion, referred to herein as "LUVETs." Methods of preparing LUVETs are described by MacDonald et al., *Biochim. Biophys. Acta*, 1061:297–301 (1991) and are further described in Example 1, part C, below. It is believed that LUVETs are particularly useful for encapsulating mCRP because the vesicles are formed under physically mild conditions involving an extrusion process that does not significantly influence protein structure chemically or physically. It is also believed that LUVETs are particularly useful for administering mCRP because LUVETs do not contain traces of organic solvents and detergents commonly used in preparing liposomes. Also, LUVETs are defined by a single lipid bilayer, contain relatively large internal volumes, and typically have greater encapsulation efficiency as compared to multilamellar vesicles. Although the exact mechanism(s) by which liposomes containing mCRP function is not fully understood, it is believed that the liposomes may act as a vehicle for efficient delivery of mCRP to the cancer cells.

The mCRP is preferably administered to the mammal by injection (e.g., intravenous, intraperitoneal, subcutaneous, intramuscular). Effective dosages and schedules for administering mCRP may be determined empirically, and making such determinations is within the skill of the art. Applicants have found that a dose of from about 0.10 mg to about 20 mg of mCRP per kilogram of body weight of the mammal, and preferably from about 2 mg to about 10 mg per kilogram, is effective for treating cancer, whether the mCRP is administered in a pharmaceutically-acceptable carrier or contained in liposomes. It is understood by those skilled in the art that the dose of mCRP that must be administered will vary depending on, for example, the mammal which will receive the mCRP, the type of cancer, the extent of cancer cell growth or metastasis, the biological site or body compartment of the tumor(s), the route of administration, and the identity of any other drugs or treatment being administered to the mammal, such as radiation or surgical treatment. It is also understood that it may be necessary to give more than one dose of mCRP. Generally, multiple doses of mCRP must be given to the mammal. The interval between doses is preferably from about 1 day to about 3 days. Administration of mCRP should be continued until health has been restored to the mammal.

In accordance with another method of treating cancer in a mammal, an effective amount of mCRP is administered to the mammal in combination with another agent. The mCRP may be administered to the mammal in a pharmaceutically-acceptable carrier or in liposomes, as described above. The agent administered in combination with the mCRP may be a naturally-occurring or a synthetic substance, and preferably has anti-cancer activity.

In one embodiment of the method, the agent is a cytotoxic agent. Preferably, the cytotoxic agent is a chemotherapeutic compound known in the art. Chemotherapeutic compounds contemplated by the present invention include, but are not limited to, Thiotepa, Busulfan, Cyclophosphamide, Methotrexate, Cytarabine, Bleomycin, Cisplatin, Doxorubicin, Melphalan, Mercaptopurine, Vinblastin, and 5-Fluorouracil. Other chemotherapeutic compounds are listed in Krakoff, *CA-A Cancer Journal For Clinicians*, 41:264–278 (1991), incorporated herein by reference. Typically, cytotoxic agents function in destroying cells and/or preventing their multiplication and are thus, useful in treating cancer. Although not fully understood, it is believed that mCRP may protect against adverse toxic effects associated with or resulting from such chemotherapeutic compounds by stimulating host defenses.

In another embodiment of the method, the agent is an immunoadjuvant or cytokine. Immunoadjuvants and cytokines, also referred to as "biological response modifiers," are known in the art. Generally, such molecules are useful in stimulating or enhancing host defense mechanisms and are therefore useful in anti-cancer therapy. Examples of immunoadjuvants or cytokines that may be administered include interferon(s), colony stimulating factor (CSF), tumor necrosis factor (TNF), hormones such as steroids, and interleukins such as IL-1, IL-2, and IL-6.

The agent is preferably administered in a pharmaceutically-acceptable carrier such as water, saline, or buffer. The agent may be administered to the mammal orally or by injection (e.g., intravenous, intraperitoneal, subcutaneous, intramuscular). It is within the skill in the art to determine acceptable carriers and proper means of administering the agent. The mCRP and agent may be administered by the same means or by different means. For instance, mCRP may be administered to the mammal by intravenous injection while the agent is administered orally to the mammal.

Effective dosages and schedules for administering mCRP are described above. Effective dosages and schedules for administering the agent in combination with mCRP may be determined empirically, and making such determinations is within the skill in the art. Prior to administering the agent and mCRP, it is preferable to determine toxicity levels of the agent(s) so as to avoid deleterious effects. Depending on the agent administered, the agent and mCRP may have additive or synergistic activity. For instance, administration of mCRP may reduce the effective dosage of agent to be administered. It will be understood by those persons skilled in this art that the dose of agent administered will vary, depending on, for example, the mammal being treated, the type of cancer, the systemic location of the cancer, and the amount of mCRP being administered to the mammal. Generally, multiple doses of agent must be administered in combination with mCRP. It is also preferable that the agent is administered at time intervals different from mCRP administration. Preferably, the agent is administered about 4 hours to about 8 hours before or after administering mCRP. Administration of the agent and mCRP should be continued until health has been restored to the mammal.

The invention also relates to a method of identifying cancer cells in a mammal using mCRP as an imaging agent. To identify the cancer cells, mCRP is administered to the mammal by injection (e,g, intravenous, intraperitoneal, subcutaneous, intramuscular). mCRP then localizes to the cancer cell sites and binds to the cancer cells, as described further in Examples 2 and 3 below.

In one embodiment, labeled mCRP may be administered to the mammal. Labels useful in the method are well known in the art and include but are not limited to, enzymes, fluorophores, radioisotopes, and biotin-avidin. The labels can then be readily detected by techniques known in the art.

Alternatively, a labeled component that binds to the mCRP may be administered to the mammal. For instance, enzyme-labeled or fluorescein-labeled antibodies having specific reactivity for mCRP epitopes may be administered to the mammal to identify and detect the presence and location of cancer cells to which the mCRP has bound.

EXAMPLES

Example 1: Anti-Tumor Activity of mCRP Against EMT6 Breast Adenocarcinoma

In vivo experiments were performed to determine whether mCRP demonstrates anti-tumor activity against EMT6, a murine breast adenocarcinoma. The activity of mCRP was evaluated by examining primary tumor growth and metastases.

A. CRP Preparation and Purification

Human ascitic fluids were obtained from the Cytology Division of the Department of Pathology, Northwestern Memorial Hospital, Chicago, Ill., and Evanston Hospital, Evanston, Ill. Using sterile techniques, the fluids were filtered through filter fluff, and $CaCl_2$ was then added to a final concentration of 2–5 mM. The fluid-$CaCl_2$ mixtures were stored at 4° C.

Each fluid was sampled and analyzed in a radial immunodiffusion assay for CRP according to a modification of the method described by Crowle, *Immunodiffusion*, Academic Press, New York, Chapter 3 (1973). Ascitic fluids having CRP concentrations >25 μg/ml were purified by sequential calcium dependent affinity chromatography, with modifications to the methods described by Volanakis et al. [*J. Immunol.*, 126:1820–1825 (1981)] and de Beer et al. [*J. Immuno. Methods*, 50:17–31 (1982)]. Approximately 3–4 liters of fluid were applied to a phosphorylcholine substituted Bio-Gel A 0.5 m (BioRad, Richmond, Calif.) affinity column with a 325 ml column volume over 36–48 hours. The column was washed exhaustively with equilibration buffer (75 mM Tris-HCl, 150 mM NaCl, 2 mM $CaCl_2$, pH 7.3) until eluant absorbance at 280 nm was <0.05. CRP-containing fractions, having absorbance at 280 nm≧0.25, were then eluted by Tris-citrate chelation buffer (75 mM Tris-HCl, 7.5 mM citrate, 150 mM NaCl, pH 7.3).

CRP fractions were pooled and diluted 3-fold with deionized distilled water and adjusted to pH 7.3. The diluted fractions were then applied to a DE-52 anion exchange column (Whatman Biochemicals, Kent, England) at a ratio of 50 g resin for every 500 ml of diluted CRP. Next, CRP-containing fractions were eluted with a linear 0.05–0.5M NaCl gradient in 10 mM Tris-HCl, pH 7.3. To remove residual SAP, the fractions were applied to an unsubstituted Bio Gel A 0.5 m column (BioRad) and eluted with the equilibration buffer above. The CRP was tested and confirmed negative for IgG and SAP by radial immunodiffusion (RID), and confirmed negative for IgM, IgE, and complement components C1q and C3 by a double diffusion assay.

Protein concentration was determined by a modification of the bicinchoninic acid (BCA) protein assay (Pierce Chemical Co., Rockford, Ill.) as described by Sorenson et al. [*Experientia*, 42:161–162 (1986)], and by a spectrophotometric absorbance assay at 215 nm and 225 nm as described by Waddell [*J. Lab. Clin. Med.*, 48:311–314 (1956)]. Total CRP content was calculated by using the extinction coefficient of 1.95 $cm^{-1}$ (mg/ml) for CRP at 280 nm [Wood et al.,

*J. Clin. Invest.*, 30:616–622 (1951)]. The purity of CRP was calculated by dividing the total amount of CRP by the total amount of protein in the same sample and multiplying by 100. The protein purity of CRP was determined from these calculated values to be ≧98.5%.

CRP purity was also confirmed by sodium dodecyl sulfate-polyacrylamide gel electrophoresis (SDS-PAGE) under reducing conditions using a 4.0% stacking gel, a 12.0% resolving gel, and the buffer systems described by Laemmli, *Nature*, 227:680–685 (1970). The gels were run at 4° C. with constant voltage settings of 100 V until the dye front completely entered the stacking gel. The gel was thereafter run at 200 V to completion. All CRP protein migrated as a single band of approximately 22.5 Kd and was evaluated by laser densitometry on an UltroScan XL densitometer (LKB Instruments) to be greater than 99% pure.

The purified CRP was concentrated to 1 mg/ml by Ultrafiltration under nitrogen using an Amicon PM-30 membrane (Amicon, Danvers, Mass.) and dialyzed against Tris buffered saline-calcium (10 mM Tris-HCl, 150 mM NaCl, 2 mM $CaCl_2$, pH 7.3). The CRP was then sterile filtered sequentially through a 0.45 micron and 0.2 micron Acrodisc filter assembly (Gelman Sciences, Ann Arbor, Mich.) and stored at 4° C. in sterile glass vials.

B. mCRP Preparation

Modified CRP ("mCRP") was prepared using the method previously described by Potempa et al. [*Mol. Immunol.*, 20:1165–1175 (1983); *Mol. Immunol.*, 24:531–541 (1987)]. Purified native CRP, prepared as described above, at 1 mg/ml in Tris-buffered saline calcium buffer, was chelated with 5 mM EDTA and incubated in 8M urea for 2 hours at 37° C. Urea was then removed by dialyzing against low ionic strength Tris buffered saline (10 mM Tris-HCl, 50 mM NaCl, pH 7.3). It is preferable to prepare mCRP in low ionic strength buffer so as to minimize aggregation of the mCRP. mCRP concentrations were then determined using the extinction coefficient of 1.95 $cm^{-1}$ (mg/ml) at 280 nm and the BCA protein assay, as described above. The mCRP was sterile filtered as described above and stored in low ionic strength Tris buffered saline at 4° C. in sterile glass vials.

C. LUVET Preparation

LUVETs containing either native CRP or mCRP (prepared as described above), or control buffer, were prepared according to a modification of the method reported by MacDonald et al., *Biochim. Biophys. Acta*, 1061:297–301 (1991). More particularly, the method employed was a combination of two previously described methods—a first method that utilized mild conditions for the entrapment of biologically active macromolecules [Kirby et al., *Liposome Technology, Volume I, Preparation of Liposomes*, CRC Press, pp. 19–27 (1984)] and a second method to form vesicles of well defined size and homogeneity [Olson et al., *Biochim. Biophys. Acta*, 557:9–23 (1979)].

A mixture of L-α-lecithin (phosphatidylcholine), sphingomyelin, (Avanti Polar Lipids, Inc., Pelham, Ala.) and cholesterol (Sigma) was placed in a round bottom flask in a molar ratio of 1:1:1 and dissolved in HPLC grade chloroform (Sigma). A total of 35.5 mg of these lipid components were suspended in 6.75 ml chloroform and dried under high vacuum in a 50° C. water bath using a rotary evaporator (Buchi Roto-vac, Bern, Switzerland) for at least one hour to form a thin film on the walls of the flask. The dried lipid content was then hydrated with 3.5 ml of the aqueous phase media to be encapsulated (i.e., native CRP, mCRP, or control buffer) to form a lipid concentration of 15.9 mM.

The vesicles that spontaneously formed were subjected to nine extrusions under pressure through a single 0.1 micron polycarbonate membrane (Nucleopore, Pleasanton, Calif.) mounted in a hand-driven extrusion apparatus [developed in the laboratories of R. C. MacDonald and described in MacDonald et al., *Biochim. Biophys. Acta*, 1061:297–301 (1991)] fitted with two 0.5 ml Hamilton syringes (Hamilton, Reno, Nev.). An odd number of extrusion passages were performed to avoid possible contamination during hydration of the sample and from large vesicles which might not have passed through the filter on the first pass. The LUVETs from the extrusion process had a homogeneous and well defined size distribution of approximately 0.1 micron. The LUVETs were stored at 4° C. for a period of one to two hours.

The amount of protein, either native CRP or mCRP, encapsulated in the LUVETs was determined by an adaptation of the procedure described by Kaplan et al., *Meth. Enzymol.*, 172:393–399 (1989). At room temperature, 20 μl of each LUVET sample was diluted with 2.0 ml of distilled deionized water. To the diluted sample, in sequence, was added the following: 200 μl of 10% (w/v) SDS, 300 μl of Tris-SDS (1M Tris-HCl, 1% (w/v) SDS, pH 7.5) and 600 μl of 10% trichloroacetic acid (TCA). After each addition, the mixture was vortexed continuously for ten seconds. The mixture was allowed to incubate for five minutes at room temperature after the TCA step.

Each sample was filtered onto a Millipore HAWP 090 00 filter (Millipore Corporation, Bedford, Mass.) and washed with 2.0 ml of 6% (w/v) TCA. After washing, the filter was placed in 200 ml of Amido Black staining solution [0.1% (w/v) Amido Black 10 B (Bio-Rad) dissolved in methanol/ glacial acetic acid/water at a ratio of 45:10:45] for 3 minutes on a shaker table. The filter was removed and washed with approximately 200 ml of distilled deionized water for 2 minutes on a shaker table. The filter was then blotted and minced with a clean razor blade before it was placed in 700 μl of Amido Black elution buffer (25 mM NaOH, 0.05 mM EDTA, 50% Ethanol). The dye was eluted from the filter with occasional vortexing during thirty minutes of incubation at room temperature, and the eluate absorbance was measured at 630 nm. Absorbance values were used to calculate the protein concentration from linear standard curves generated with samples containing 2–24 μg BSA.

LUVET encapsulation efficiency was determined by the calcein volume phase assay (to determine the internalized volume) and Amido Black protein assay (to determine the quantity of protein). Encapsulation efficiency was also determined using a fluorescent aqueous phase volume marker as described by Oku et al., *Biochim. Biophys. Acta*, 691:332–340 (1982). The amount of native CRP measured, expressed as a lipid ratio, was 2.0 μg CRP/μmol of lipid. The vesicle internalization volume, also expressed as a lipid ratio, was 2.02 μl/μmol lipid. The calculated LUVET encapsulation efficiency was 990 μg CRP/ml±20 μg/ml internal volume.

The LUVETs were also evaluated for antigenic determinants characteristic for native CRP and mCRP to determine whether the LUVETs contained homogeneous native CRP or mCRP preparations or whether there was interconversion of these CRP forms. To determine and quantitate the presence of specific native CRP or mCRP antigenic determinants, LUVETs containing either native CRP, mCRP, or control buffer were analyzed by a Dot-enzyme-linked immunofiltration assay ("Dot-ELIFA"). The Dot-ELIFA [described by Clark et al., *J. Biotechniques*, in press (1992)] was developed by an adaptation of previously described protocols [Hawkes et al., *Analyt. Biochem.*, 119:142–147 (1982); Pappas et al., *J. Immunol. Meth.*, 64:205–214

(1983)]. This assay utilizes nitrocellulose membranes instead of plastic microtiter plates, and thus is particularly useful with proteins like CRP which are known to undergo conformational changes when absorbed to plastic surfaces [See, Potempa et al., *Mol. Immunol.*, 24:531–541 (1987)].

Briefly, serial dilutions of native CRP, mCRP, and LUVETs containing either native CRP, mCRP, or control buffer were applied to 0.45 micron nitro-cellulose membranes through an Easy-Titer™ unit (Pierce Chemical Co., Rockford, Ill.). All wells were washed with 100 µl sample buffer to remove unbound protein. The remaining unbound sites were blocked with a back coat of bovine serum albumin (BSA). The nitrocellulose membrane was then placed in a Fast Blot Developer™ unit (Pierce Chemical Co.).

Next, the membrane was incubated with primary antibody specific for native CRP or mCRP. The following monoclonal antibodies ("mAbs"), obtained from Dr. Lawrence Potempa, Immtech International, Inc., Evaston, Ill., were tested: 15.1D6 (reactivity specific for native CRP); 13.3H12, 26.7A8, and 26.8C10 (reactivity specific for mCRP); and 15.2C10 (reactivity for native CRP and mCRP). These antibodies are described in co-pending application Ser. No. 07/374,166, and in Ying et al., *J. Immunol.*, 143:221–228 (1989).

After washing to remove unbound primary antibody, the membrane was incubated with goat or horse anti-mouse-IgG horseradish peroxidase (HRP) conjugate. The membrane was then washed to remove unbound secondary antibody, and developed with a HRP substrate.

Results of Dot-ELIFA testing confirmed that mAb 13.3H12 is specific for mCRP epitopes and mAb 15.1D6 is specific for native CRP epitopes. The results also showed that <1% of the native CRP encapsulated in LUVETs displayed mCRP epitopes recognized by mAb 13.3H12. Accordingly, <1% of the native CRP had been converted to mCRP via the LUVET extrusion procedure. Although it was believed unlikely that mCRP encapsulated in LUVETs would result in conversion to the native CRP form, LUVETs containing mCRP were examined for reactivities with 13.3H12 and 15.1D6 antibodies. The results showed that essentially no native CRP epitopes were expressed for the LUVETs containing mCRP.

For comparison, multilamellar vesicles ("MLVs") containing native CRP were prepared according to the methods described by Deodhar et al., *J. Biol. Resp. Modifiers*, 1:27–34 (1982). The MLVs containing native CRP were then examined for CRP and mCRP epitopes using Dot-ELIFA analysis, as described above.

In a dose dependent manner, the MLV preparations displayed antigenic determinants recognized by both mAb 13.3H12 and mAb 15.1D6. The quantity of 15.1D6 detected was greater than 13.3H12 at all titration points examined up to an MLV aliquot containing 2048 ng of native CRP. Overall, the data indicated that about 40% of the native CRP encapsulated in MLVs by the methods reported by Deodhar et al. was converted to mCRP.

The encapsulation efficiency of these MLVs was also evaluated using the calcein volume phase assay and the Amido Black protein assay. In these MLV preparations, the amount of CRP, reported as a ratio to lipid, was 0.28 µg CRP/µmol of lipid. The MLV internalized volume, reported as a volume to lipid ratio, was 0.82 µl/µmol of lipid. Using the CRP protein/lipid ratio from the Amido Black protein assay, and the volume/lipid ratio from the calcein volume phase assay, the MLV encapsulation efficiency was 341.5 µg CRP/ml±53 µg/ml internal volume.

Some of the properties of MLVs as compared to LUVETs are shown in Table 1 below.

TABLE 1

| | Multilamellar Vesicles (MLVs) | Large Unilamellar Vesicles (LUVETs) |
| --- | --- | --- |
| Amount protein/lipid | 0.28 µg/µmol lipid | 2.0 µg/µmol lipid |
| Internalization Volume | 0.82 µl/µmol lipid | 2.02 µl/µmol lipid |
| Encapsulation Efficiency | 341.5 ± 53 µg CRP/ml | 990 ± 20 µg CRP/ml |

As shown in Table 1, the LUVETs yielded greater amounts of protein encapsulated per lipid amount, as well as greater internalization volume and encapsulation efficiency. Also, native CRP encapsulation in LUVETs resulted in no detectable conversion of native CRP to mCRP. Thus, it was concluded that LUVETs were superior to MLVs.

D. In Vivo Toxicity Study of mCRP

Prior to administering native CRP, mCRP, or LUVETs containing either native CRP, mCRP, or control buffer to the test animals, an in vivo toxicity study was performed to determine whether administration of mCRP is accompanied by harmful side-effects.

A total of 80 female BALB/c mice (obtained from Harlan Laboratories, Madison, Wis.), 10–12 weeks of age, were randomly divided into control and experimental groups of five mice each. Experimental groups were injected with mCRP dosages ranging from 1 µg/mouse to 100 µg/mouse while control groups were injected with phosphate-buffered saline. Injections were either intravenous, intraperitoneal, or subcutaneous and were administered on Days 4, 11, and 18.

Prior to the first injection, baseline data on all experimental and control group animals was recorded. The animals were monitored with tri-weekly measurements of body weight and urinalysis for blood, protein, glucose, and pH (Ames Co., Hema-combistix Reagent Strips). The majority of animals, 75 of 80 (>93%) increased or maintained body weight values within commonly accepted variation limits, which are defined as no body weight loss greater than 10% of the original body weight. A total of 5 out of 80 animals decreased in total body weight by values >than 10% of the original body weight. Of this group, no mouse experienced a decrease in body weight exceeding 24%.

To determine the significance of the differences between the mean values of the percent change in body weight of the control group compared to each experimental group, the two-tailed Student t-test was used with $p < 0.05$ considered to be significant. Test results showed that there was no statistically significant difference in percent change in body weight for all groups.

Urinalysis testing revealed minimal variation for the measured parameters for all groups tested. At no time was glucose or blood detected in the urine. The protein content of the urine for all animals was consistently measured at 30 µg/ml without exception. The urine pH values varied minimally within normal limits and never exceeded more than a single pH unit in variation for any individual animal.

In addition, general appearance and activity of all groups were photographed and recorded. Observable activity and grooming were within normal limits, including a tendency for the phenomenon of barbering exhibited by all animals within three separate cages. All of these results demonstrate that mCRP administered at the various doses and by various routes of administration described does not elicit harmful side-effects as measured by the described parameters.

E. Effects of Native CRP and mCRP on EMT6 Primary Tumor Growth and Metastasis

An in vivo tumor growth assay was performed to determine the effects of mCRP and LUVETs containing either native CRP, mCRP, or control buffer, on the growth of murine EMT6 breast adenocarcinoma tumors. The murine breast adenocarcinoma cell line, EMT6, was obtained from Dr. John Wilson, Medical College of Virginia, Richmond, Va., and cultivated in RPMI-1640 medium supplemented with 10% heat-inactivated fetal calf serum, 11.25 μg/ml L-glutamine, 100 U/ml penicillin, 100 μg/ml streptomycin, and 2.5 μg/ml amphotericin B. The cell line was tested and determined to be free of mycoplasm and other microbial contamination.

On Day 1 of the study, approximately $3 \times 10^6$ viable EMT6 cells/0.10 ml RPMI-1640 were injected into BALB/c mice obtained from Harlan Laboratories, Madison, Wis. The cells were injected subcutaneously proximal to the calcaneus of the right hind limb of all the animals and the animals were randomly divided into seven groups as listed in Table 2 below. On Day 7, tumor mass had grown in all the animals.

Calculated tumor volume reflects tumor burden. Each test group contained 15–16 animals. Mean tumor burdens were calculated per treatment group and were compared using the two tailed Student t-test with p values <0.05 considered to be statistically significant.

Figure 1:
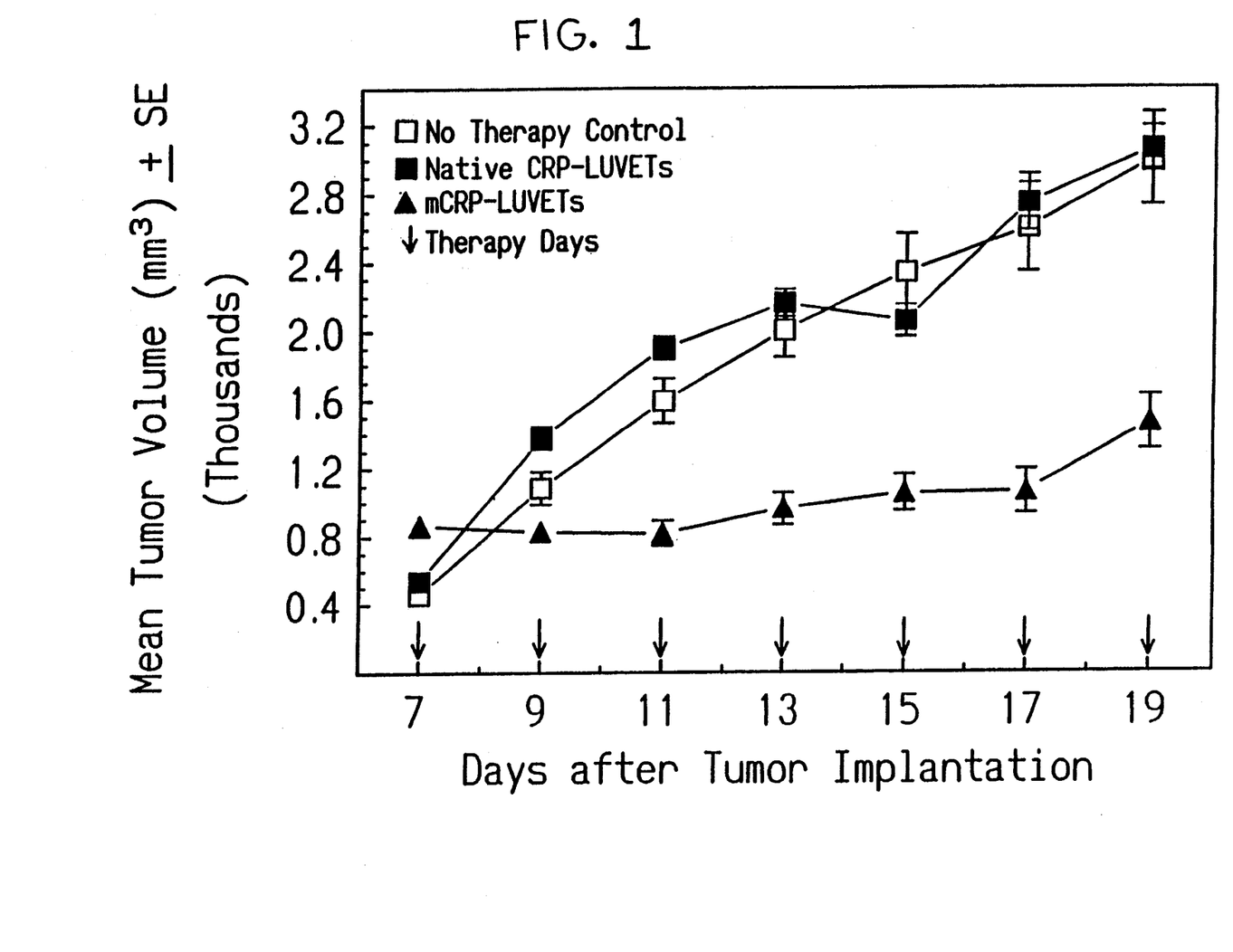
FIG. 1 is a graph illustrating a comparison of the effects of mCRP (in LUVETs) treatment, native CRP (in LUVETs), and no therapy on murine EMT6 breast adenocarcinoma primary tumor volume during Days 7–19 of the study.

The growth of the primary tumors in animals receiving mCRP in LUVETs (Group 5) as compared to animals receiving no therapy (Group 1) and animals receiving native CRP in LUVETs (Group 4) is shown in FIG. 1 for days in which therapy was administered. The intravenous therapy injections were made on the days indicated by the arrows shown in FIG. 1.

Seven days after tumor implantation, mean tumor mass in the various groups varied from 459 mm³ to 863 mm³. Tumor growth rate is plotted as mean tumor volume in cubic millimeters, ±standard error of the mean. Tumors in animals receiving native CRP in LUVETs continued to grow at a rapid rate, paralleling and not significantly different from that rate observed with animals in the no therapy control group. In contrast, tumor growth rate in animals receiving mCRP in LUVETs was minimal throughout this time period. Using the Student's t-test, tumor growth in mCRP in LUVETs treated animals was significantly different from

TABLE 2

| Group | Treatment-i.v. Injection on Days 7, 9, 11, 13, 15, 17, 19 | Total Number of Animals | Number of Animals with Necrosis on Day 29 | Number of Animals with Tumor Volume Increase/Decrease During Study | Number of Animals with Metastatic Lung Tumors on Day 29 | Animal Death During Study Period |
|---|---|---|---|---|---|---|
| 1 | None - Control | 15 | 0 | 15/0 | 8 | 1 |
| 2A | Low ionic strength buffer | 5 | 0 | 5/0 (4/1)² | 5 | 0 |
| 2B | LUVETs in standard ionic strength buffer | 5 | 0 | 5/0 | 5 | 0 |
| 2C | LUVETs in low ionic strength buffer | 5 | 0 | 5/0 | 2 | 2 |
| 3 | 100 μg mCRP (in low ionic strength buffer) | 15 | 7 (1)¹ | 15/0 (10/5)² | 6 | 0 |
| 4 | 100 μg native CRP (in LUVETs) | 15 | 1 (1)¹ | 15/0 (9/6)² | 10 | 3 |
| 5 | 100 μg mCRP (in LUVETs) | 16 | 12 (14)¹ | 9/7 (0/16)² | 1 | 1 |

¹Additional number of animals displaying necrotic lesion of questionable nature.
²Animals with consistent tumor volume increase/animals with fluctuating tumor volume.

Treatments described in Table 2 for each group were administered by intravenous injection every second day for 13 days, beginning on Day 7. Prior to injection, the LUVETs containing native CRP, mCRP, or control buffer were subjected to separation chromatography on a disposable 2.5 ml Bio-Gel A 0.5 m column (approximately 1–2 ml bed volume/mg protein) to remove non-LUVET associated native CRP or mCRP. The LUVETs passed through the column with the void volume and was turbid in appearance. Protein that was not encapsulated was measured as a slow moving fraction with absorbance at 280 nm eluting from the column at a 2–3 column volume interval from the LUVET fraction.

As described by Mcintosh et al., Cancer Research, 49:1408–1414 (1989), growth of tumor at the primary site of initiation was assessed by measuring along the shortest and longest dimensions of the raised tumor mass to the nearest 0.05 mm using a vernier caliper. The smaller radius (a) and the larger radius (b) were used to calculate tumor volume in mm³ using the formula of a prolate ellipsoid:

$$Volume = 4/3 \pi a^2 b$$

tumor growth in the no therapy control animals to p <0.025 on Day 9, and p <0,001 on Days 11–19.

Figure 2:
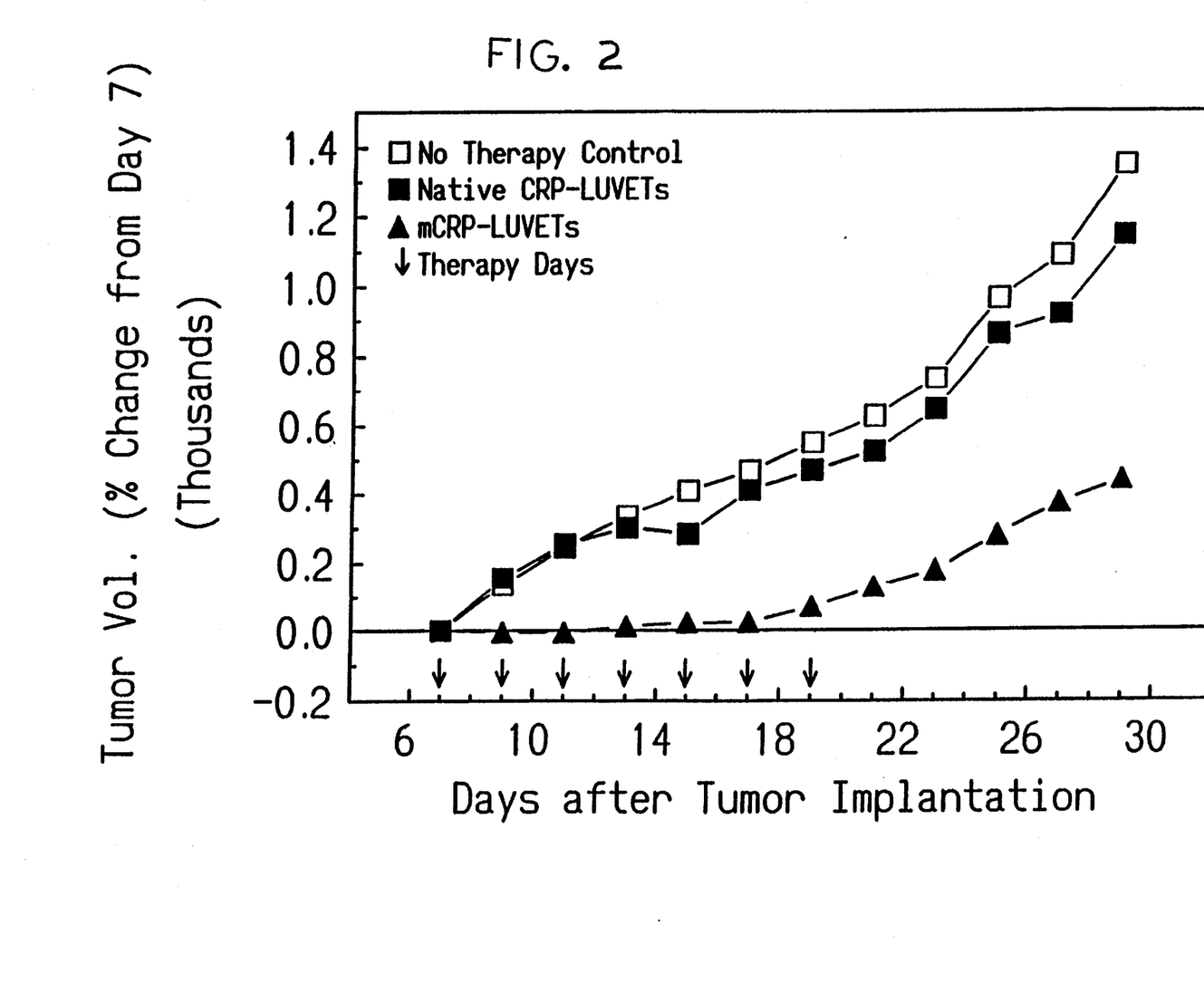
FIG. 2 is a graph illustrating a comparison of the effects of mCRP (in LUVETs) treatment, native CRP (in LUVETs) treatment, and no therapy on murine EMT6 breast adenocarcinoma primary tumor percent changes of volume for Days 7–29 of the study.

Once therapy was stopped (after Day 19) through Day 29, tumor growth in the native CRP in LUVETs treated animals was unaffected, continuing at a rapid rate. As seen in FIG. 2 in which tumor growth is plotted as the percentage change from that tumor size measured on Day 7, tumors in both the no therapy control group and the native CRP in LUVETs group were greater than 10-times larger (1000%) than those tumors measured on Day 7. Tumor growth in the mCRP in LUVETs group increased after therapy was stopped, growing at a rate which was comparable to that rate observed with tumors of a similar size in the no therapy control group.

Assuming a linear growth rate and using least squares linear regression analysis for tumor growth on days of therapy compared to days after therapy (summarized in Table 3 below), the no therapy control group animal tumor growth rate was 203.5±12.7 mm³/day during Days 7–19 and 366.9±34.1 mm³/day during Days 19–29. Native CRP-LUVETs group animal tumor growth rate was 186.8±24.4 mm³/day during therapy and 367.0±33.7 mm³/day on Days 19–29. The mCRP in LUVETs group animals had negligible average tumor growth of 44.7±12.0 mm³/day during therapy days, Days 7–19, and the growth rate increased to 327.6±18.1 for Days 19–29.

TABLE 3

CHANGE IN TUMOR VOLUME (mm³/day)*

| Therapy | Days 7–19 | Days 11–19 | Days 19–29 |
| --- | --- | --- | --- |
| No therapy control | 203.5 ± 12.7 | — | 366.9 ± 34.1 |
| Native CRP (in LUVETs) | 186.8 ± 24.4 | — | 367.0 ± 33.7 |
| mCRP (in Buffer) | 67.3 ± 22.9 | 15.0 ± 24.4 | 369.8 ± 12.0 |
| mCRP (in LUVETS) | 44.7 ± 12.0 | — | 327.6 ± 18.1 |

*as calculated by least squares linear regression analysis

Tumor growth increased upon cessation of mCRP in LUVETs therapy to a rate similar to control group animals. Nonetheless, mCRP in LUVETs treated animals continued to have tumors which were statistically smaller than those tumors measured in either the no therapy control group or the native CRP in LUVETs therapy group to p <0.01 at all time points from Days 21–29.

Figure 3:
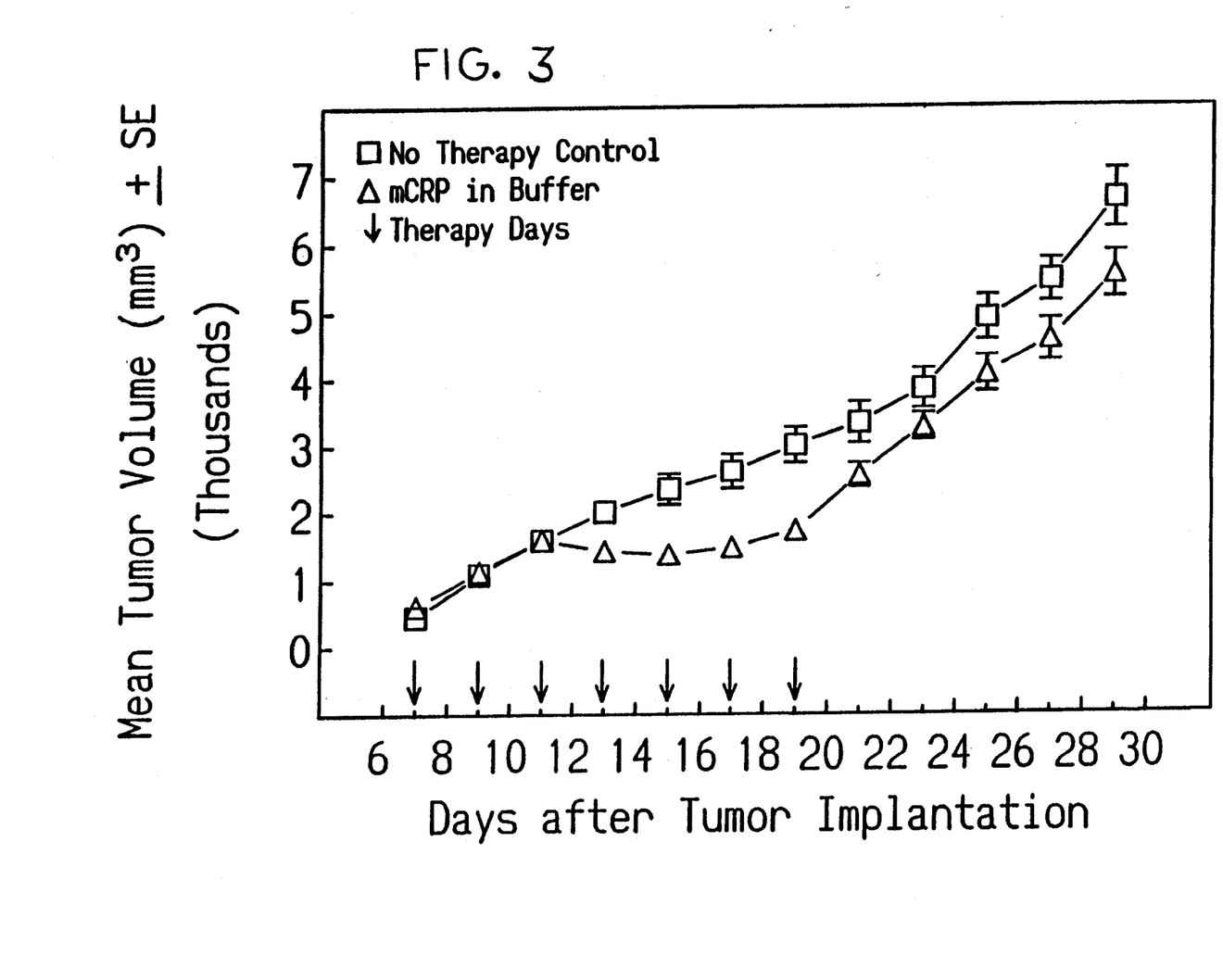
FIG. 3 is a graph illustrating a comparison of the effects of mCRP and no therapy on the EMT6 breast adenocarcinoma primary tumor volume for Days 7–29 of the study.

In FIG. 3, the mCRP treated group (Group 3, receiving mCRP in buffer) is compared to the no therapy group (Group 1) with regard to tumor growth (mean tumor volume) over the 29 day course of the study. The results show that mCRP was also effective in preventing growth of the murine breast adenocarcinoma tumors. mCRP did not show an immediate protective effect commencing with the first therapeutic dose, as was observed with the mCRP in LUVETs therapy (Group 5). On Days 9 and 11, measured mean tumor volume in the mCRP therapy group increased in parallel with the no therapy control group (and the native CRP in LUVETs group) animals. After administration of the third mCRP-buffer dose, at a time when mean tumor volume had reached approximately 1500 mm³, mCRP therapy became effective, resulting in no further mean tumor growth in treated animals for the remainder of the therapy period (through Day 19). The tumor growth rate for all therapy days (7–19) was 67.3±22.9 mm³/day, a 50% greater rate than the mCRP in LUVETs therapy group. (Table 3) However, if linear regression is performed on tumor growth rate for only those days when mCRP-buffer therapy appeared to effect tumor growth (Days 11–19), the growth rate reduces to 15.0±24.2 mm³/day. Using the two tailed Student's t-test for significance, this tumor growth rate is not significantly different from a zero growth rate.

Figure 4:
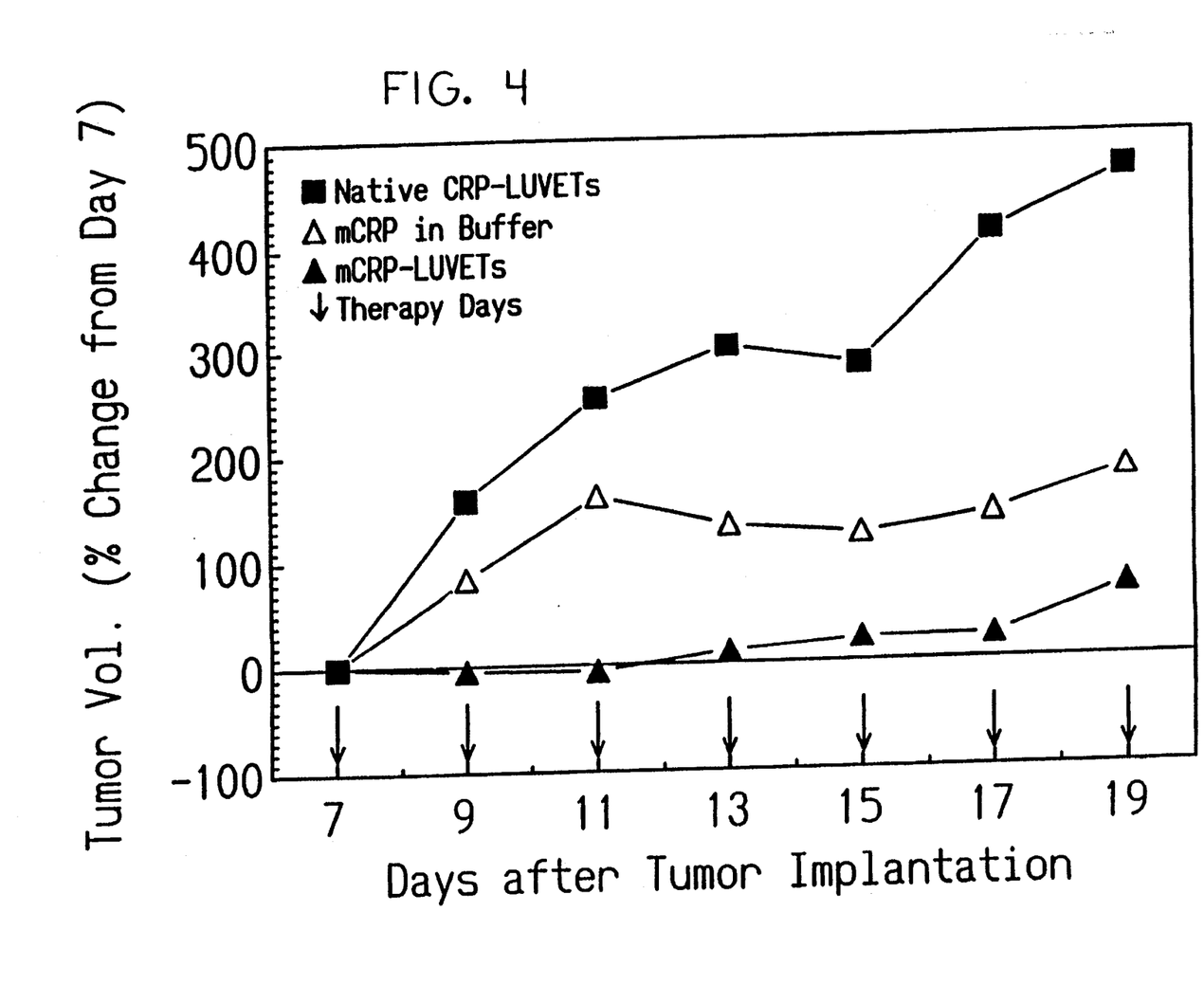
FIG. 4 is a graph illustrating a comparison of the effects of mCRP, mCRP in LUVETs, and native CRP in LUVETs, on the percent changes of tumor volumes of the murine EMT6 breast adenocarcinoma primary tumor.

After Day 19, tumor growth increased at a rate comparable to that measured in groups not showing effective anti-tumor activity. When mean tumor volumes are plotted as percentage change from that tumor size measured on Day 7 (FIG. 4), animals receiving mCRP therapy did show a slight retardation of tumor growth during the first three days of therapy compared to native CRP in LUVETs therapy (and no therapy control). From Days 11 to 19, essentially no mean tumor growth occurred. On Day 13, mCRP therapy was significantly different from the no therapy control or native CRP in LUVETs therapy to a p value of <0.025. On Days 15–19, measured differences continued to be significant to p <0.001 compared to both groups. After therapy was stopped and tumors began growing again (Days 21–29), mean tumor volumes in the mCRP therapy group continued to be significantly different from the native CRP-LUVETs therapy group to p <0.001 until Day 23, falling off to p <0.02 by Day 29.

These data suggest mCRP, not native CRP, is an effective therapy in preventing the growth of murine breast adenocarcinoma. Furthermore, mCRP is effective whether injected in liposomes or alone in buffer.

To more completely characterize mCRP anti-tumor effects, data on the number of animals exhibiting necrotic lesions, progressive versus fluctuating tumor growth rates, number of lung metastases, and number of individual animal deaths in each group were determined. These data are shown in Table 2 above.

Tumor sites were visually examined throughout the study for necrotic lesions. Visual examination of tumors on Day 7 indicated the presence of a raised, subdermal solid tumor mass with well-defined borders having uniform color and texture over the entire surface of the tumor. A necrotic lesion was defined as a blackening of the skin surface with possible involution of tissue. No animal in any control group (30 total animals—Groups 1, 2A, 2B, and 2C) showed signs of necrosis. In contrast, 12 (possibly 14) of 16 animals treated with mCRP in LUVETs, and 7 (possibly 8) of 15 animals treated with mCRP showed necrosis, while 1 (possibly 2) of 15 animals receiving native CRP in LUVETs therapy showed necrosis. Six of 15 animals receiving mCRP in LUVETs therapy developed necrotic sites on Day 9, 48 hours after initial treatment. By Day 19, some animals in this therapy group showed two or three separate lesions. The necrotic lesions were soft and pliable to palpation and were well-defined subdermal marks covering up to one-third of the whole tumor surface. A fine needle aspiration biopsy was performed on one necrotic site which verified dead tumor cells and a preponderance of polymorphonuclear leukocytes and macrophages at the site. Also, analysis of the biopsy indicated the observed necrosis was not the result of an infectious process.

The necrotic lesions were of variable size and shape and did not exceed 15 mm at the largest measured dimension. While the initially recognized lesions were malleable by palpation, with time they became nonpliable to touch and hirsute with retraction, with slightly sunken borders. When tumors were resected at necropsy, additional discrete focal necrotic lesions were discovered within tumor mass not visible by surface examination. No other organs or tissues were found to be abnormally affected by mCRP therapy (mCRP in buffer or mCRP in LUVETs), indicating mCRP has a direct anti-tumor effect while being non-toxic.

The growth characteristics of the tumors in individual animals also exhibited important differences between the various groups listed in Table 2. For example, six out of the 15 animals in Group 5 were documented to have reductions in tumor size up to a 60% decrease when compared to tumor volume prior to therapy on Day 7 (greater than one half decline in tumor size). Furthermore, tumor growth in 44% of animals (7/16) in Group 5 showed a fluctuating progression in tumor growth.

In contrast, measurement of primary tumor growth in both control groups (Groups 1, 2A, 2B, and 2C receiving no native CRP or mCRP) showed consistent tumor growth with little variation among animals (only one tumor-bearing animal in Group 2A showed a fluctuating increase in tumor size). Tumor growth in animals receiving LUVETs containing control buffer (Groups 2B and 2C) showed that the LUVETs themselves did not have an inhibitory effect on primary tumor growth. The rate of tumor growth in both control groups was also comparable. The number of animals exhibiting consistent tumor volume increases/fluctuating increases in the other two groups were: Group 3 (mCRP in buffer treatment)(10/5); and Group 4 (native CRP-LUVETs treatment)(9/6).

Lung tissues of all the dissected animals were also evaluated for metastases. As shown in Table 2, control Groups 1 and 2 had a high incidence of metastases—20 out of 30 animals (67%) comprising Groups 1 and 2 had metastatic tumor growth in the lungs. More specifically, of the 15 animals comprising Groups 2A, 2B, and 2C, 12 animals (80%) had observable metastatic lung tumors. Group 4 animals (receiving native CRP in LUVETs) also showed a relatively high incidence of metastasis. In Group 4, 10 out of 15 (67%) animals had lung metastases.

In contrast, Group 3 and Group 5 animals receiving mCRP or mCRP in LUVETs, respectively, showed reduced incidence of metastases. In Group 3, 6 out of 15 (40%) animals had lung metastases, while lung metastatic tumors were observed in only 1 (6.25%) out of 16 animals in Group 5.

The data from this in vivo study thus revealed that mCRP and mCRP in LUVETs treated animals had a higher incidence of tumor necrosis, and greater decrease, or fluctuation, in tumor size. The results also suggest that mCRP reduces metastasis of the tumor, in addition to the effects on primary tumor growth.

Example 2: Binding of Native CRP and mCRP To EMT6 Breast Adenocarcinoma Cells

To determine whether native CRP or mCRP binds EMT6 tissue culture cells, cytospin slides were prepared using a cytocentrifuge. Cultured EMT6 cells, described in Example 1, part E, were washed and resuspended in phosphate buffered saline (PBS) to approximately $1-2\times10^6$/ml. Glass microscope slides with card covers were mounted in a cytocentrifuge and 0.2–0.3 ml of the EMT6 cell suspension placed in the reservoir. The cells were then affixed to the slides by centrifugation for 15 minutes. The resulting cell monolayer was air dried for 30 minutes and stored at room temperature.

The slides were then overlaid with 200 µl of native CRP or mCRP in buffer, described in Example 1, parts A and B, diluted to 100 µg/ml, and incubated for 30 minutes in a humidified chamber at 37° C. Next, the slides were rinsed in two changes of PBS, and preincubated with blocking solution [1% bovine serum albumin (BSA), 0.5% normal horse serum in PBS] for 15 minutes. After two washes with PBS, biotinylated primary antibody solution, mAb15.1D6 (described in Example 1) at 4 µg/ml or biotinylated polyclonal antibody LP5 [obtained from Dr. Lawrence Potempa, Immtech International, Inc., Evanston, Ill., and described in Potempa et al., *Mol. Immunol.*, 24:531–541 (1987)] at 10 µg/ml was added for a 30 minute incubation in a humidified chamber at 37° C. Antibodies were biotinylated using a modification of the protocols described by Kendall et al., *J. Immunol. Meth.*, 56:329–339 (1983) and Hsu et al., *J. Histochem. Cytochem.*, 27:1131–1145 (1981).

The slides were washed twice with PBS and streptavidin-horseradish peroxidase secondary reagents were applied. Next, diaminobenzidine substrate buffer [6 mg of DAB tetrahydrochloride (Sigma) in 10 ml of PBS, plus 0.1 ml of 3% $H_2O_2$] was prepared and filtered to remove precipitate. Slides were then immersed in the buffer for 15 minutes. The reaction was stopped by washing in running water for 10 minutes. After washing, the slides were counterstained by immersion in Mayer's Hematoxylin (Sigma) for 3 minutes and rinsed in water to remove excess staining solution before addition of 30 mM $NH_4OH$ for 20 seconds. The slides were again washed in water and mounted with a glass coverslip using Permount.

Incubation of EMT6 cytospin slides with either native CRP or mCRP showed direct binding of both native CRP and mCRP to EMT6 cells. After incubation with 10 µg/ml native CRP, the EMT6 cells bound 15.1D6 mAb (5.5 µg/ml) preferentially to 13.3H12 mAb (5.5 µg/ml). The staining pattern for bound 15.1D6 appeared to be membrane associated, particularly the cell membrane and to a less extent, the nuclear membrane. This staining pattern was negated by competitive inhibition studies with native CRP at 10 µg/ml concentrations and seemingly unaffected by mCRP at 10 µg/ml.

Cytospin slides incubated with 10 µg/ml mCRP followed by either 13.3H12 or 15.1D6 mAbs, showed binding to 13.3H12, not 15.1D6. The staining pattern with 13.3H12 was membrane associated and appeared to display some diffuse nuclear specificity.

Example 3: In Vivo Localization of Native CRP and mCRP To Human Lung Adenocarcinoma Tumor Sites An in vivo study was conducted to determine whether native CRP and mCRP localize to tumor sites in animals bearing lung adenocarcinoma tumors.

The human lung adenocarcinoma cell line, A549 (obtained from the American Type Culture Collection, Rockville, Md.), was cultured in RPMI-1640 medium supplemented with 10% heat-inactivated fetal calf serum, 11.25 µg/ml L-glutamine, 100 U/ml penicillin, 100 µg/ml streptomycin, and 2.5 µg/ml amphotericin B. After culturing, the cells were washed twice in RPMI-1640 and resuspended at a concentration of $3\times10^6$ viable tumor cells/0.10 ml. Then, 0.10 ml of the cell suspension was injected into 6–8 week old BALB/c nude (athymic) mice (obtained from Harlan-Sprague-Dawley Laboratories, Madison, Wis.) subcutaneously proximal to the foot pad of the right hind limb.

By Day 7, palpable tumor growth could be measured. The animals were then randomly divided into four groups of animals, one animal per group, as shown below in Table 4.

TABLE 4

| | Treatment | |
|---|---|---|
| Group | Day 7 | Day 8 |
| 1 | 100 µl sterile saline | — |
| 2 | 500 µg mAb 443A6 | — |
| 3 | 500 µg mAb 443A6 | 100 µg native CRP |
| 4 | 500 µg mAb 443A6 | 100 µg mCRP |

On Day 7, monoclonal antibody 443A6 was injected. mAb 443A6, which specifically binds A549 lung adenocarcinoma cells, was obtained from Dr. James A. Radosevich, Northwestern University Medical Center, Chicago, Ill. The antibody is also commercially available from Affinity BioReagents, Inc., Neshanic Station, N.J. Preparation of mAb 443A6 and its activity is further described in U.S. Pat. No. 4,816,402 and Radosevich et al., *Cancer Research*, 46:5808–5812 (1985). For Groups 2, 3 and 4 receiving antibody treatment, 500 µg of mAb 443A6 was diluted in 1.0 ml ascites fluid and 100 µg was injected intravenously while 900 µl was injected intraperitoneally.

The following day, Day 8, either 100 µg native CRP or mCRP (prepared as described in Example 1, parts A and B) was injected intravenously into the animals. Approximately 990 minutes to 2 hours later, the animals were sacrificed. The tumors were then resected and contralateral leg skeletal muscle, liver, spleen, and lung tissue samples were excised from the sacrificed animals.

Frozen tissue sections were prepared by dissecting a small sample of tissue, about 0.5 cm$^{-3}$, and immediately submerging it in a gelatin mixture of polyvinyl alcohol, polyethylene glycol, and dimethyl benzyl ammonium chloride pooled on a square of aluminum foil. The capsule thus formed was frozen gradually on dry ice before the foil was wrapped and stored at −80° C.

Prior to sectioning, clean glass slides were coated with 0.005% poly-L-lysine (diluted in 500 ml deionized water and filtered). The slides were submerged in the filtered solution for 15 minutes, and removed and air dried for 30 minutes before use or storage. Tissue sections of approximately 8 microns were collected on the coated slides, air dried at room temperature for 30 minutes, and then stored at −70° C.

For staining, the glass slides with the affixed tissue sections were allowed to warm to room temperature and then submersed in tap water for 2 minutes. To mask endogenous peroxidase activity, the tap water incubation was followed by a 0.03% $H_2O_2$-PBS solution incubation for 15 minutes. The tissue sections were then reacted with biotinylated mAbs specific to native CRP or biotinylated polyclonal antibodies specific for mCRP, blocked, and stained, as described in Example 2 above.

The staining pattern showed that mAb specific for native CRP was reactive with excised tumor tissue sections from A549 tumor-bearing BALB/c nude mice which received native CRP injections. Likewise, polyclonal antibody specific for mCRP was reactive with the tumor tissue excised from the mice that received a mCRP injection. Tumor tissue from the mice receiving native CRP did not demonstrate any mCRP reactivity when probed with the mCRP specific polyclonal antibody. Also, native CRP reactivity was not detected in the tumor tissue from the mice receiving mCRP. The biotinylated antibodies were not reactive with other excised tissues from the host animals (lung, spleen, skeletal muscle) except for liver tissue. Reactivity with the liver tissue was not unexpected, however, because of endogenous biotin in the liver. In summary, specific antigenic determinants, corresponding to the specific form of CRP (either native CRP or mCRP) administered intravenously, localized to the parenchyma of the previously established A549 primary tumor at levels readily detectable by common immunohistochemical techniques.

In addition to evaluating tumor tissue sections, A549 tissue culture cells were evaluated by preparing cytospin slides as described in Example 2. Incubation of the A549 cytospin slides with either native CRP or mCRP, each conjugated with fluorescein isothiocyanate, showed direct binding of both native CRP and mCRP to the cells. Furthermore, A549 cells incubated with either native CRP or mCRP displayed antibody reactivity with mAb 15.1D6 and mAb 13.3H12, respectively.

Example 4: Use of mCRP and 5-Fluorouracil To Treat P388 Leukemia In Vivo

An in vivo study was performed to determine the effects of treating P388 tumor bearing animals with mCRP in combination with 5-Fluorouracil.

Female CD2-$F_1$ mice (a BALB/c×DBA/2 $F_1$ hybrid obtained from Taconic Farms, Germantown, N.Y.), were housed under standard laboratory conditions and fed commercial laboratory rodent chow (Purina). Housing was maintained at 64° to 72° F. with a 12 hour light/dark cycle. All other conditions were maintained as described in the *Guide for the Care and Use of Laboratory Animals* (NIH Publication No. 86–23, Revised 1985). For purposes of the study, the animals were divided into 10 groups, as shown in Table 5 below.

TABLE 5

| Group # | Number of Animals in Group | Chemotherapeutic Agent Treatment | mCRP Dose | mCRP Carrier |
|---|---|---|---|---|
| 1 | 20 | — | — | — |
| 2 | 6 | — | — | Low ionic strength PBS |
| 3 | 6 | — | — | Standard PBS |
| 4 | 10 | 5-FU (20 mg/kg) | — | — |
| 5 | 6 | — | 50 μg | Low ionic strength PBS |
| 6 | 6 | — | 200 μg | Standard PBS |
| 7 | 6 | 5-FU (20 mg/kg) | 50 μg | Low ionic strength PBS |
| 8 | 6 | 5-FU (20 mg/kg) | 200 μg | Standard PBS |
| 9 | 6 | 5-FU (10 mg/kg) | 50 μg | Low ionic strength PBS |
| 10 | 6 | 5-FU (10 mg/kg) | 200 μg | Standard PBS |

P388 leukemia cells (obtained from the American Type Culture Collection, Rockville, Md.) were passaged twice as an intraperitoneal implant of 1×106 cells in DBA/2 mice. After the second passage, the cells were concentrated to 1×10$^6$/0.1 ml of diluted ascitic fluid and on Day 1 of the study, were injected intraperitoneally to the CD2-$F_1$ mice.

Two dosages of 5-Fluorouracil ("5-FU") (Sigma) were prepared by dissolving 5-FU in sterile distilled water to a concentration of 1.0 mg/ml and 2.0 mg/ml. As shown in Table 5, either 10 mg or 20 mg 5-FU/kg body weight was injected intraperitoneally on Days 2–6 in the morning. The volume of 5-FU injected for each animal was based upon their respective Day 2 body weight.

On Days 2–6 in the afternoon, mCRP was injected intravenously into Group 5–10 animals, as shown in Table 5. mCRP was obtained from Dr. Lawrence Potempa, Immtech International, Inc., Evanston, Ill., and prepared as follows. CRP was prepared as described in Example 1, part A. To make mCRP, the CRP at 1 mg/ml was incubated in 8M ultra-pure urea (Schwartz-Mann, Spring Valley, N.Y.) in the presence of 10 mM EDTA for one hour at 37° C. The urea was removed by dialysis into 10 mM sodium phosphate buffer (pH 7.4) containing 0.015M sodium chloride.

The mCRP was sterile filtered through a 0.20 micron filter (Gelman). The concentration was then adjusted to 0.5 mg/ml with 10 mM sodium phosphate buffer, pH 7.4, containing 0.015 sodium chloride to produce a solution of mCRP for the low dose (50 μg) mCRP administration in a 0.1 ml volume.

Some of the sterile filtered soluble mCRP was adjusted to physiological ionic strength by adding sodium chloride to give a final concentration of 0.15M NaCl and then incubated in an ice bath for 15 minutes. The majority of this mCRP preparation self-aggregated to form an opalescent solution which was centrifuged to about 5000×g for 10 minutes to sediment the protein. The sedimented protein was resuspended in sterile 10 mM sodium phosphate buffer, pH 7.4, containing 0.15M NaCl to give a final concentration of 2 mg/ml. This mCRP was administered as the high dose (200 μg) mCRP treatment in a 0.1 ml volume.

Body weights of all animals were recorded on Day 2 and

Day 6, using an AND electronic balance (AND Company, Ltd., Tokyo, Japan) which was calibrated prior to use. All animals weighed between 12.1 gm and 19.0 gm at Day 2 of the study.

Figure 5:
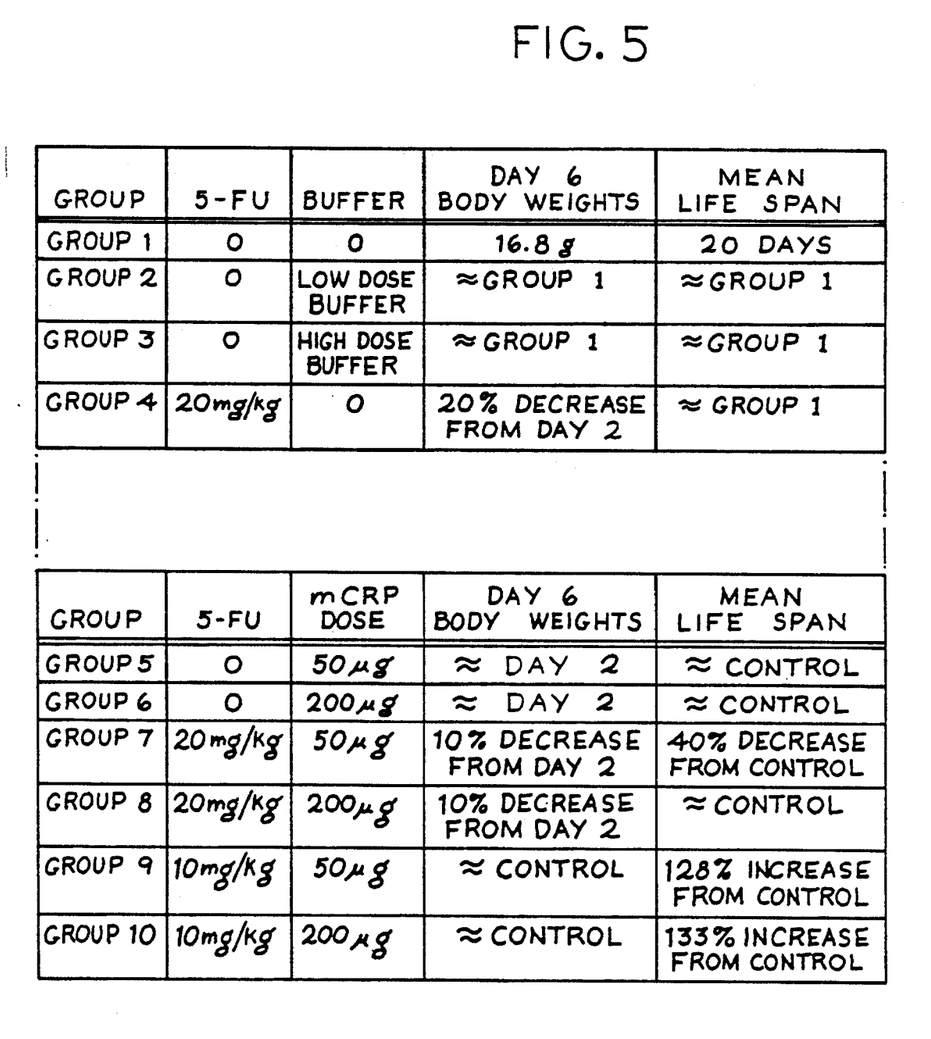
FIG. 5 shows a comparison of the effects of 5-Fluorouracil and mCRP treatment on body weight and life span of P388 tumor bearing animals.

As shown in FIG. 5, the mean body weight for Group 1, receiving no therapy, was 16.8 g at Day 6 of the study. The mean body weight of Group 2 (15.2 g) and Group 3 (16.6 g) animals receiving low dose and high dose buffer was not considered to be different from untreated control animals. Administration of 50 µg of mCRP (Group 5) did not alter the mean body weight of animals at Day 6. Similarly, administration of 200 µg of mCRP (Group 6) did not exhibit toxicity as determined by change of body weight on Day 6.

Administration of 20 mg of 5-FU (Group 4) decreased body weight by 20% on Day 6. The combination of a chemotherapeutic drug at a theoretical optimum dose with the administration of mCRP at low dosage (Group 7) decreased body weight by 10% at Day 6. Combination therapy with the high dose of mCRP (Group 8) was not toxic to the animals as determined by a 10% decrease in body weight. Combination therapy at sub-optimal doses of 5-FU with either high dose (Group 9) or low dose (Group 10) mCRP likewise did not elicit toxicity based on body weight analyses.

The mean life span of control Group 1 animals was 20 days. The life span of animals administered low dose (Group 2) or high dose (Group 3) buffer was not different from Group 1 control tumor bearing mice. Administration of 5-FU at 20 mg/kg body weight (Group 4) did not dramatically alter the life span of the tumor bearing animals. Administration of mCRP at either 50 µg (Group 5) or 200 µg (Group 6) also did not alter the life span of tumor bearing animals.

Combination therapy of 20 mg/kg 5-FU with 50 µg of mCRP (Group 7) decreased the life span of animals by 40%.

In contrast, the combination with 200 µg of mCRP (Group 8) did not alter the life span of animals relative to the control groups. However, combination therapy of 10 mg of 5-FU/kg body weight with 50 µg or 200 µg of mCRP (Groups 9 and 10), increased life span by 128% and 133%, respectively.

Five animals, out of 18 animals from the mCRP therapy combination groups (Groups 8, 9, and 10), survived until the end of the study. One animal from the 5-FU treatment group (Group 4) also survived until the end of the study. Presence of leukemia cells in the surviving animals was examined by performing peritoneal lavage on anesthetized animals on Day 31. First, saline was injected into the peritoneal cavity, withdrawn and processed. A cell count was performed, and then cytospin slides were prepared. The cytospin slides were stained with hematoxylin and eosin and evaluated. The surviving animals were then sacrificed in accordance with American Veterinary Medical Association guidelines.

The results of peritoneal lavage cell counts and cytospin evaluations are shown below in Table 6. Examination of the peritoneal cells from animals that survived up to Day 31 indicated that the surviving animal in Group 4 was a "no take." This was based on the absence of leukemia cells in the peritoneal cavity. Leukemia cells were still present in the peritoneal cavity of the surviving animals from Groups 8, 9, and 10. The number of leukemia cells, however, indicated that administration of mCRP in combination with 5-FU inhibited tumor cell proliferation. Additionally, there was a normal complement of endogenous nucleated cells indicating that the mCRP did not alter the types of cells normally found in the peritoneum.

TABLE 6

EXAMINATION OF PERITONEAL LAVAGE CYTOSPIN PREPARATIONS

| | Preparation # | Leukemia Cell Count | | Non-Leukemia Cell Count (Nucleated) | |
|---|---|---|---|---|---|
| | | Relative | Absolute | Relative | Absolute |
| Group 4 20mg/kg5-FU | 69A | 0 | 0 | 1 Eosinophil 12 Lymphocyte 39 Macrophage 2 Mast cells 45 Mesothelial 1 Neutrophil | $3.6 \times 10^6$ |
| Group 8 20 mg/kg 5-FU 200µgmCRP | 55A | 23 | $0.25 \times 10^6$ | 1 Eosinophil 12 Lymphocyte 39 Macrophage 45 Mesothelial | $0.85 \times 10^6$ |
| | 62A | 95 | $2.81 \times 10^8$ | 2 Lymphocyte 3 Macrophage | $0.15 \times 10^8$ |
| Group 9 10 mg/kg 5-FU 50µgmCRP | 48A | 88 | $5.72 \times 10^7$ | 5 Macrophage 7 Neutrophil | $0.78 \times 10^7$ |
| Group 10 10 mg/kg 200µmCRP | 66A | 94 | $1.09 \times 10^8$ | 1 Lymphocyte 2 Macrophage 3 Mesothelial | $0.07 \times 10^8$ |
| | 39A | 97 | $1.26 \times 10^8$ | 5 Macrophage 7 Neutrophil | $0.04 \times 10^8$ |

For relative cell counts, n = 100 cells total count per preparation

What is claimed is:

1. A method of screening for cancer cells in a mammal comprising administering modified-CRP to the mammal and detecting the modified-CRP bound to the cancer cells.

2. The method of claim 1 wherein the modified-CRP is labeled to allow for its detection when bound to the cancer cells.

3. The method of claim 1 wherein a labeled component that specifically binds modified-CRP is administered to the mammal to allow for detection of modified-CRP bound to the cancer cells.

4. The method of claim 1 wherein the cancer is adenocarcinoma.

5. The method of claim 2 wherein the modified-CRP is labeled with a label selected from the group consisting of radioisotopes and biotin-avidin.

* * * * *